(12) United States Patent
Wang et al.

(10) Patent No.: US 10,660,536 B2
(45) Date of Patent: May 26, 2020

(54) WEARABLE BIOMETRIC MEASUREMENT DEVICE

(71) Applicant: Huami Inc., Sunnyvale, CA (US)

(72) Inventors: Fei Wang, Fremont, CA (US); Ting Chen, San Jose, CA (US)

(73) Assignee: Huami Inc., Cupertino, CA (US)

( * ) Notice: Subject to any disclaimer, the term of this patent is extended or adjusted under 35 U.S.C. 154(b) by 743 days.

(21) Appl. No.: 14/854,569

(22) Filed: Sep. 15, 2015

(65) Prior Publication Data

US 2017/0071483 A1 Mar. 16, 2017

(51) Int. Cl.
*A61B 5/0452* (2006.01)
*G16H 40/63* (2018.01)
(Continued)

(52) U.S. Cl.
CPC .......... *A61B 5/0452* (2013.01); *A61B 5/0404* (2013.01); *A61B 5/14551* (2013.01);
(Continued)

(58) Field of Classification Search
CPC ... A61B 5/0404; A61B 5/0006; A61B 5/0428; A61B 5/6898; A61B 2505/07; A61B 2560/045; A61B 2560/0468; A61B 2562/0261; A61B 5/0022; A61B 5/0402; A61B 5/04028; A61B 5/0408; A61B 5/04085; A61B 5/0002; A61B 5/01;
(Continued)

(56) References Cited

U.S. PATENT DOCUMENTS 5,289,824 A 3/1994 Mills et al.
5,978,693 A 11/1999 Hamilton et al.
(Continued)

FOREIGN PATENT DOCUMENTS

CN 201585990 U 9/2010
CN 203122371 U 8/2013
(Continued)

OTHER PUBLICATIONS

Martini et al., A real time adaptive filtering approach to motion artifacts removal from ECG signals, IJBET, 3(3-4), 2010, DOI: 10.1504/IJBET.2010.032694, 13 pages.

*Primary Examiner* — Christopher A Flory
*Assistant Examiner* — Vynn V Huh
(74) *Attorney, Agent, or Firm* — Young Basile Hanlon & MacFarlane, P.C.

(57) ABSTRACT

A wearable biometric measurement device includes a ring body having interior and exterior surfaces, an electrocardiogram component including first and second electrodes wherein a single lead electrocardiogram is formed upon contact with the first electrode and the second electrode, a pulse oximeter component including a light emitter and a photodetector wherein the photodetector receives one or more signals transmitted by the light emitter, and a communication component. A system for measuring and processing biometric data includes a wearable biometric measurement device, a monitor device, and a server. A method for measuring biometric data using a wearable biometric
(Continued)

measurement device includes pre-processing biometric signals, feature extraction on the signals, and event prediction with respect to the signals.

18 Claims, 4 Drawing Sheets

(51) Int. Cl.
*A61B 5/00* (2006.01)
*A61B 5/0404* (2006.01)
*A61B 5/1455* (2006.01)
*A61B 5/01* (2006.01)
*A61B 5/0245* (2006.01)

(52) U.S. Cl.
CPC .............. *A61B 5/681* (2013.01); *A61B 5/726* (2013.01); *G16H 40/63* (2018.01); *A61B 5/0002* (2013.01); *A61B 5/01* (2013.01); *A61B 5/0245* (2013.01); *A61B 5/4818* (2013.01); *A61B 5/7207* (2013.01); *A61B 5/7275* (2013.01); *A61B 5/742* (2013.01)

(58) Field of Classification Search
CPC . A61B 5/0245; A61B 5/0452; A61B 5/14551; A61B 5/4818; A61B 5/681; A61B 5/7207; A61B 5/726; A61B 5/7275; A61B 5/742; A61B 5/00; G06F 19/30
See application file for complete search history.

(56) References Cited

U.S. PATENT DOCUMENTS

| | | |
|---|---|---|
| 8,315,695 B2 | 11/2012 | Sebelius et al. |
| 8,433,399 B1 | 4/2013 | Nosrati et al. |
| 8,509,882 B2 | 8/2013 | Albert et al. |
| 2006/0100530 A1* | 5/2006 | Kliot ............... A61B 5/0002 600/483 |
| 2010/0090798 A1* | 4/2010 | Garcia Molina .... G06K 9/0055 340/5.53 |
| 2012/0022336 A1* | 1/2012 | Teixeira ............... A61B 5/0205 600/300 |
| 2012/0123232 A1* | 5/2012 | Najarian ............ A61B 5/0022 600/345 |
| 2012/0203124 A1 | 8/2012 | Lim |
| 2013/0281815 A1* | 10/2013 | Varadan ............ A61B 5/04085 600/388 |
| 2014/0221866 A1* | 8/2014 | Quy ...................... H04W 4/21 600/544 |
| 2015/0297134 A1* | 10/2015 | Albert .................. A61B 5/681 600/384 |

FOREIGN PATENT DOCUMENTS

| | | |
|---|---|---|
| DE | 10201217919 | 3/2014 |
| WO | WO2013112979 A1 | 8/2013 |
| WO | WO2013155196 A2 | 10/2013 |
| WO | WO2014022906 A1 | 2/2014 |

* cited by examiner

WEARABLE BIOMETRIC MEASUREMENT DEVICE

FIELD OF THE DISCLOSURE

This disclosure relates in general to a wearable device for measuring biometric signals.

BACKGROUND

Persons at risk for various diseases may wish to monitor certain vital, or biometric, data, for example, to identify disease risk factors and predict diagnoses. Components for performing tests typically performed by traditional electrocardiograph, pulse oximeter, and other devices as may be used for these tasks are becoming increasingly convenient due to their inclusion in wearable objects, such as wristbands and belt buckles. However, these objects can prove cumbersome as it is not always easy for a user to take satisfactory biometric measurements, and they generally only offer one type of biometric measurement (e.g., only one of heartrate and oxygen saturation). For example, a user may want to have access to heart rate, electrocardiogram, and oxygen saturation measurements at the same time.

SUMMARY

The following presents a simplified summary of the specification in order to provide a basic understanding of some aspects of the specification. This summary is not an extensive overview of the specification. It is intended to neither identify key or critical elements nor delineate the scope of such aspects. Its purpose is to present some concepts of this disclosure in a simplified form as a prelude to the more detailed description that is presented later.

Disclosed herein is a wearable biometric measurement device including a ring body having interior and exterior surfaces, an electrocardiogram (ECG) component comprising a first electrode coupled to the interior surface of the ring body and a second electrode coupled to the exterior surface of the ring body, a pulse oximeter (PO) component comprising a light emitter coupled to a first portion of the interior surface of the ring body; and a photodetector coupled to a second portion of the interior surface of the ring body, and a communication component coupled to the ring body.

Also disclosed herein is a system for measuring and processing biometric data including a wearable biometric device in accordance with the teachings herein, a monitor device, and a server, wherein the wearable biometric device is in communication with the monitor device and the monitor device is in communication with the wearable biometric device and the server.

Also disclosed herein is a method for processing biometric data collected by a wearable biometric measurement device including identifying at least one ECG signal and at least one PO signal, performing pre-processing on the at least one ECG signal and the at least one PO signal, identifying a combined biometric signal comprising the pre-processed at least one ECG signal and the pre-processed at least one PO signal, determining one or more extracted features of the combined biometric signal, and determining a predicted event based in part on the combined biometric signal and the one or more extracted features.

Details of these implementations, modifications of these implementations and additional implementations are described below.

BRIEF DESCRIPTION OF THE DRAWINGS

The description herein makes reference to the accompanying drawings wherein like reference numerals refer to like parts throughout the several views, and wherein.

DETAILED DESCRIPTION

Figure 1:
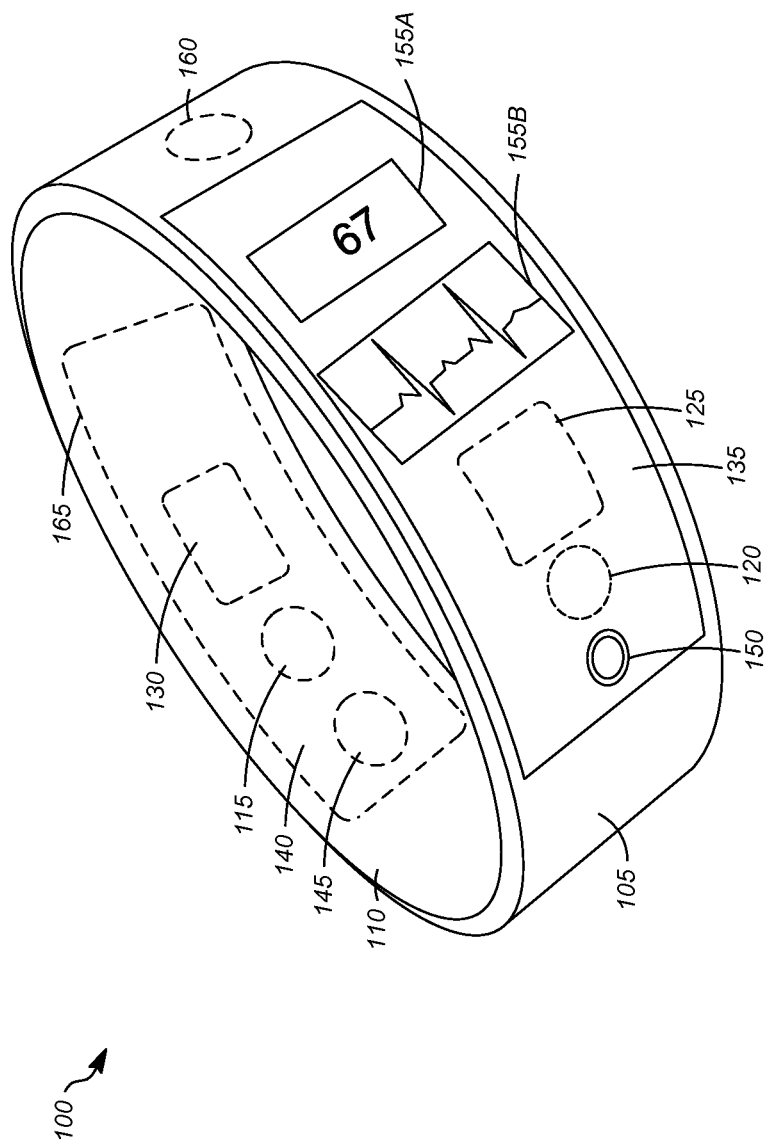
FIG. 1 is an illustration showing an example implementation of a wearable biometric measurement device according to implementations of this disclosure.

FIG. 1 depicts an example implementation of a wearable biometric measurement device 100 designed to be worn on a human user's finger as a ring capable of generally circumferentially contacting the user's finger. The body of device 100 has exterior and interior surfaces 105 and 110 wherein interior surface 110 is in communication with a user's finger while device 100 is in use. Although device 100 is shown as having a single, continuous body, other structures wearable on around human user's finger may be used.

Device 100 includes an electrocardiogram (ECG) component comprising first and second electrodes 115 and 120 configured to measuring various aspects of the user's heart function and related biometrics. First electrode 115 is coupled to interior surface 110 such that it may accurately measure various biometric signals through the user's finger. Second electrode 120 is coupled to exterior surface 105 and is not in direct contact with the finger wearing device 100. First electrode 115 and second electrode 120 are configured to identify electrical heart activity by measuring the user's pulse and transmitting the measurement data for subsequent encoding and processing. That is, upon the user contacting second electrode 120, for example, with another finger, a single lead ECG is formed, which permits device 100 to measure the user's heart activity. In an implementation, the ECG component may be selectively trained to identify specific ECG signals from the user, for example, in order to detect or diagnose specific diseases or disease risk factors.

Additionally included with device 100 is a pulse oximeter (PO) component comprising light emitter 125 and photodetector 130 configured to measuring the user's oxygen saturation. Light emitter 125 is coupled to a first portion 135 of interior surface 110 and photodetector 130 is coupled to second portion 140 of interior surface 110, wherein first and second portions 135 and 140 are generally diametric relative to interior surface 110. Light emitter 125 transmits red and infrared lights originating from red and infrared light emitting diodes through the user's finger, which lights are received by photodetector 130. Upon receipt, photodetector 130 transmits the measurement data for subsequent encoding and processing, namely, by identifying light absorption data relative to the user's finger. Unlike with the ECG component, the PO component does not require an additional step beyond wearing device 100 to take oxygen saturation measurements. In an implementation, the PO component may be configured to continuously monitor and measure the user's oxygen saturation measurements.

Further signal detection components may be included within device 100. For example, device 100 may include a thermometer component comprising temperature sensor 145 configured to measuring the user's body temperature. It will be apparent to one skilled in the art in view of this disclosure that the disposition of the further signal detection components within or on device 100 will depend on their specific nature (e.g., temperature sensor 145 is preferably coupled to interior surface 110 for maximum expose to the user's body heat). Additionally, in an implementation, LED indicator 150 may be provided to indicate when biometric measurement data is being collected.

Device 100 includes a display configured to visually represent collected biometric measurement data. In an implementation, the display may be a single output screen for visually representing all collected biometric measurement data. In another implementation, the display may be a plurality of output screens wherein each output screen visually represents a unique type of collected biometric measurement data. In another implementation, the display may be a plurality of output screens wherein any collected biometric measurement data may be visually represented on any such display. For example, and as shown in FIG. 1, the display may include two output screens wherein first output screen 155A visually represents the user's heartrate in numerical form (typically indicated as heart beats per minute) and second output screen 155B visually represents the user's pulse in graph form. The information outputted to the display may be updated as biometric measurement data is processed. Notwithstanding the implementations described herein, it will be apparent to one skilled in the art in view of this disclosure that the various biometric data measured by device 100 may be displayed on multiple displays, which may be included within one or more devices. For example, in an implementation, ECG measurement data may be shown on a display included within a wrist-worn device such as a watch or bracelet while PO measurement data may be shown on a display of device 100.

Communication component 160 permits device 100 to communicate with one or more external systems or devices, for example, to transmit biometric measurement data collected by device 100. As will be discussed in greater detail below, communication component 160 may assist a user by transmitting biometric measurement data to a medical examiner for review, diagnosis of disease, or other treatment purposes. It may further transmit data to a database or other related system for storage, such as for later review or comparison against newer collected measurements as historical data. In an implementation, communication component 160 is a Bluetooth transmitter; however, communication component 160 may operate over other suitable wireless communication systems, including without limitation an ultrasound transmitter. A printed circuit board (PCB) 165 can also be disposed within device 100. PCB 165 is capable of measuring electrical potential of device 100 and configured to electrically connect the various elements thereof. In an implementation, PCB 165 is a flexible PCB.

Notwithstanding the implementations herein described, it will be apparent to one skilled in the art in view of this disclosure that the ECG component, PO component, thermometer component, and any other components as may be utilized in connection with device 100 may be disposed within other devices. For example, each of the aforesaid components may be disposed within its own unique device, or certain combinations thereof may be disposed within unique devices, wherein each included device comprises its own communication component for transmitted signal data measured by the component(s) disposed therein. For example, in an implementation, ECG data may be measured by an ECG component disposed within a wrist-worn device such as a watch or bracelet while PO data may be measured by a PO component disposed within device 100.

Figure 2:
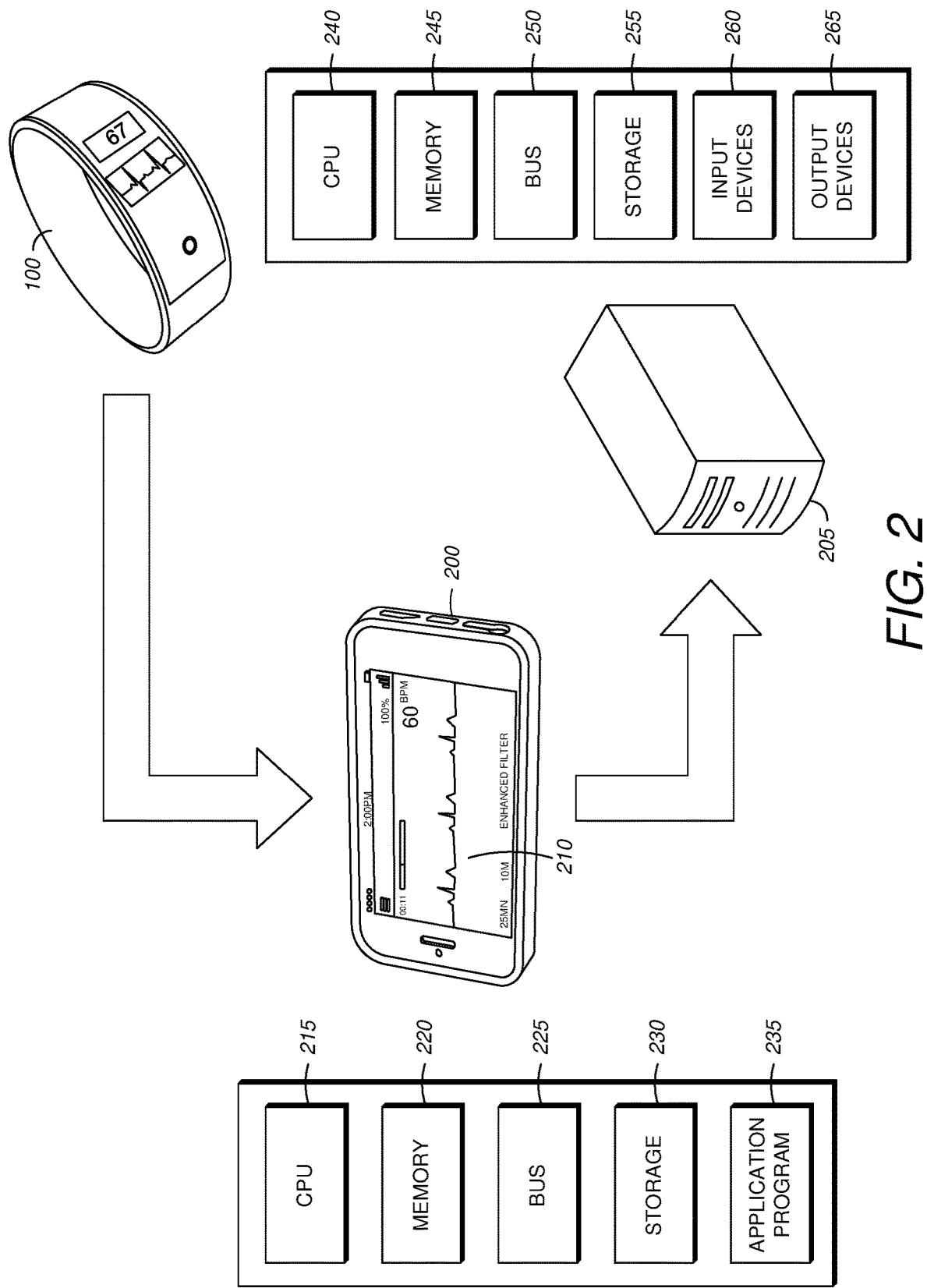
FIG. 2 is a diagram showing an example of a system configuration for a wearable biometric measurement device, monitor device, and server that may be used according to implementations of this disclosure.

FIG. 2 depicts a system configuration for communication and analysis of biometric measurements collected by a wearable biometric measurement device in accordance with the teachings herein as including device 100, monitor device 200, and server 205. In an implementation, monitor device 200 is a smartphone and server 205 is a cloud server; however, monitor device 200 may instead be any other device capable of receiving, processing, and outputting data in accordance with the teachings herein, and server 205 may instead be a physical server or other computer system.

Monitor device 200 includes display 210, which allows output to be presented to a user, for example, in response to receiving biometric measurement data from device 100 or thereafter processing such data. Display 210 may be a liquid crystal display (LCD), a cathode-ray tube (CRT), or any other output device capable of providing output from device 100. In an implementation, display 210 is a touch screen display configured to receive touch-based input, for example, in manipulating data outputted thereto.

Monitor device 200 can include a CPU 215 comprising one or more central processing units. Alternatively, CPU 215 can be any other type of device, or multiple devices, capable of manipulating or processing information now-existing or hereafter developed. Although the examples herein can be practiced with a single processor as shown, advantages in speed and efficiency may be achieved using more than one processor.

Monitor device 200 can include a memory 220, such as a random access memory device (RAM) or any other suitable type of non-transitory storage device. Memory 220 can include code and data that can be accessed by CPU 215 using bus 225. The memory can further include one or more application programs 230 and an operating system. As will be discussed in detail below, application program 230 can include software components in the form of computer executable program instructions that cause CPU 215 to perform some or all of the operations and methods described herein. A storage device 235 can be optionally provided with monitor device 200 in the form of any suitable non-transitory computer readable medium, such as a hard disc drive, a memory device, a flash drive or an optical drive.

Server 205 also includes CPU 240, memory 245, bus 250, and storage device 255, each of which being in accordance with similar features described above with respect to monitor device 200. Server 205 can include one or more input devices 260, such as a keyboard, a mouse, a microphone or a gesture-sensitive input device, receive user inputs, and can output signals or data indicative of the user inputs to CPU 240. One or more output devices 265 can be provided. One output device 265 may be a display device or a speaker.

In operation, biometric measurement data collected by device 100 can be transmitted from device 100 (e.g., by the communication component thereof) to monitor device 200, which processes the data using application program 230 (for example, as described below) and thereafter displays it for review in at least one of a processed and pre-processed form.

Monitor 200 device may also store the data for later use, such as for subsequent comparison as historical data against newer collected biometric measurement data. Monitor device 200 is configured to transmit the processed biometric measurement data to server 205. Server 205 may be accessed by one or more third process to analyze the data and provide response to the user. Server 205 may also be configured to store the data for later use similar to monitor device 200.

Although FIG. 2 depicts CPU 215 and memory 220 as being integrated into a single unit and CPU 240 and memory 245 as being integrated into another single unit, other configurations can be utilized. The operations of CPUs 220 and 240 can be distributed across multiple machines or devices (each machine or device having one or more of processors) that can be coupled directly or across a local area or other network. Memories 220 and 245 can be distributed across multiple machines or devices such as network-based memory or memory in multiple machines performing operations that may be described herein as being performed using a single computer or computing device for ease of explanation. Although a single bus 225 or 250 is depicted for each of monitor device 200 and server 205, multiple buses can be utilized. Further, storage device 255 can be a component of each of computing device 200 or can be a shared device that is accessed via a network. The system as depicted in an example in FIG. 2 thus can be implemented in a wide variety of configurations.

Figure 3:
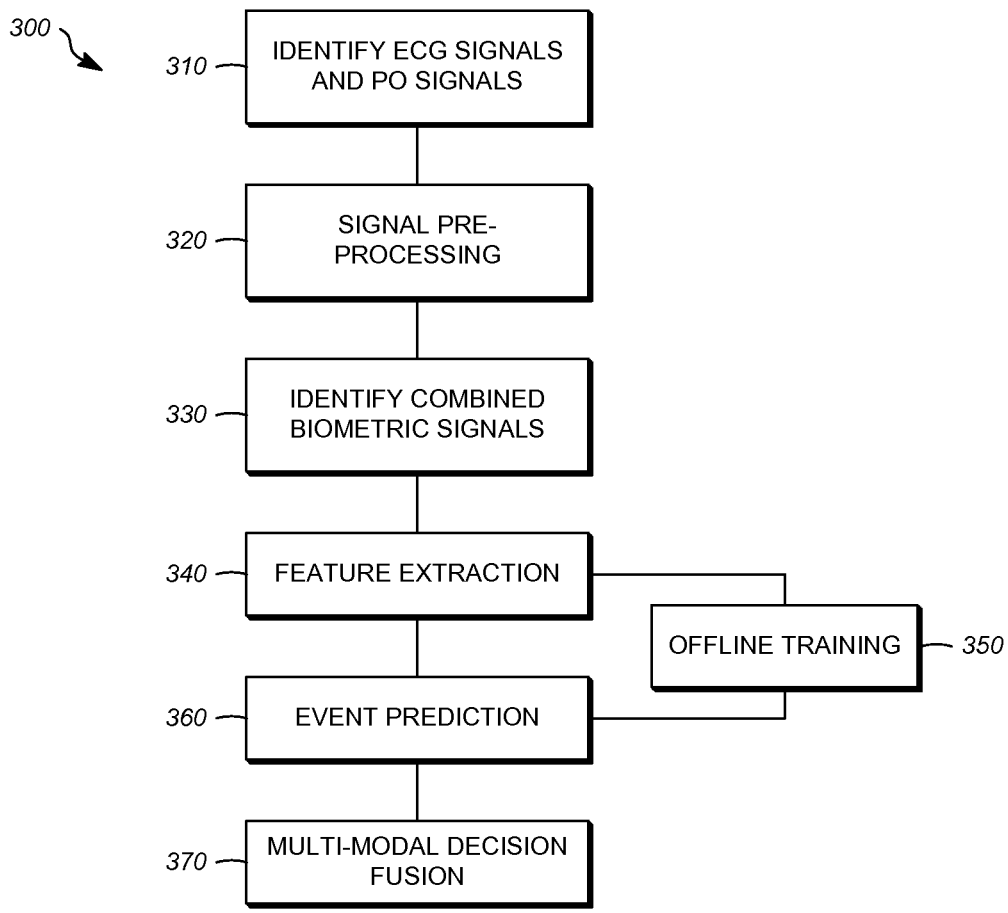
FIG. 3 is a flow chart showing an example of a process overview of biometric measurement processing according to implementations of this disclosure.

FIG. 3 is a flow chart showing an example of a method 300 for processing biometric data collected from a wearable biometric measurement device. The operations described in connection with method 300 can be performed at one or more computing devices, such as device 100, monitor device 200, or server 205. The operations described in connection with method 300 can be embodied as a storage device in the form of a non-transitory computer readable storage medium including program instructions executable by one or more processors that, when executed, cause the one or more processors to perform the operations. For example, the operations described in connection with method 300 could be application program 230 stored at memory 220 of monitor device 200 and be executable by CPU 215 of monitor device 200.

At operation 310, one or more biometric signals collected as biometric measurement data, such as from a wearable biometric measurement device, are identified. In an implementation, and as will be contemplated moving forward unless otherwise indicated, the one or more biometric signals identified are ECG signals and PO signals. These signals typically comprise raw data collected by the originating biometric measurement device (e.g., device 100) and need to be processed in order to be properly utilized to analyze the user's health and predict disease diagnosis and other events. In an implementation, specific ECG signals may be selectively measured based on training provided by the ECG component of device 100.

Figure 4:
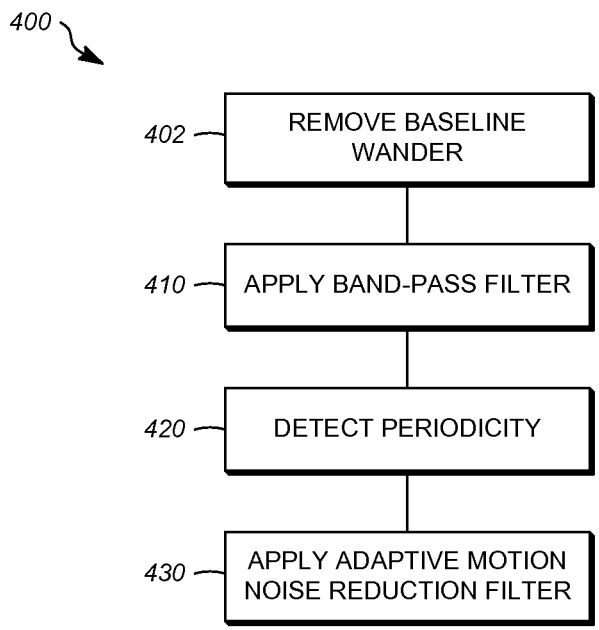
FIG. 4 is a flow chart showing an example of a process of pre-processing biometric measurement signals according to implementations of this disclosure.

At operation 320, the identified ECG signals and PO signals separately undergo signal pre-processing to prepare the subsequent analysis. FIG. 4 is a flow chart showing an example of a method 400 for pre-processing each of the ECG and PO signals. At sub-operation 402, a baseline wander, if present, is removed from the ECG, and PO signals, and, at sub-operation 410, a band-pass filter is applied thereto in order to remove any undesirable data shifts that occurred while the signals were being measured and to reduce the presence of data outside of a range to be observed (e.g., outliers). The periodicity of the ECG signals and PO signals is detected at sub-operation 420 to determine the periodic qualities of the collected measurement data. The periodicity of the ECG signals may be compared to that of the PO signals. Wherein the signals each derive from a pulse measurement, the periodicity is likely to be equal or substantially equal. The adaptive motion noise reduction filter is applied at sub-operation 430, which filter identifies motion noise included within the ECG signals and PO signals and reduces the motion noise or entirely removes it to better isolate the important data within those signals. Motion noise may include, for example, fluxes and other changes present in the ECG signals and PO signals due to the user walking, running, exercising, or otherwise moving in a manner that may interfere with a clear biometric measurement (e.g., where the user's finger moves on second electrode 120 while the ECG signals are being measured). The filter adapts to the specific form of the ECG signals and PO signals.

At operation 330, the interrelationship between the pre-processed ECG and PO signals is determined by checking the signals against each other. The pre-processed ECG and PO signals are thus merged into a single set of combined biometric signals for further processing and analysis, which will permit the subsequent operations of method 300 to yield more accurate results than if they were performed separately on the signals.

Figure 5:
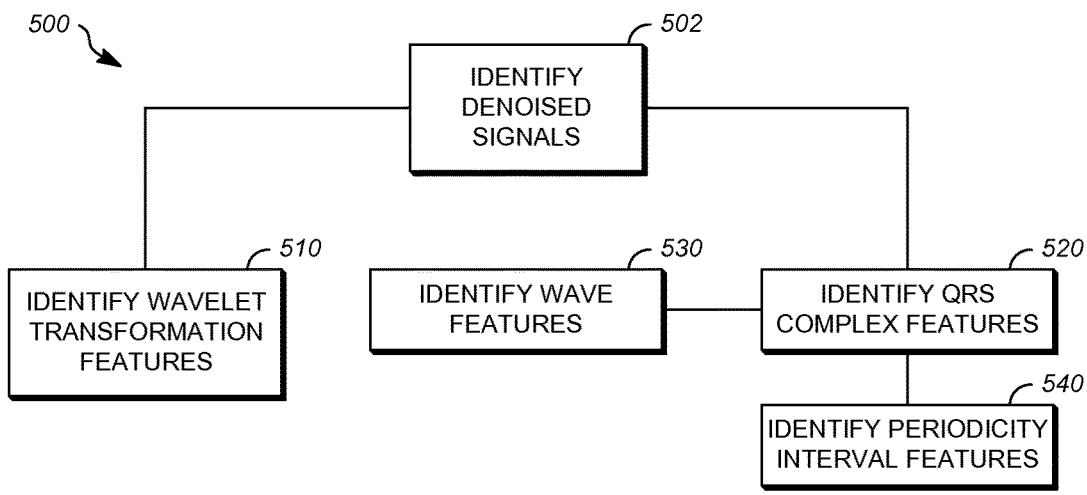
FIG. 5 is a flow chart showing an example of a process of feature extraction according to implementations of this disclosure.

At operation 340, the combined biometric signals undergo feature extraction to determine various features thereof. FIG. 5 is a flow chart showing an example of a method 500 for performing feature extraction on the combined biometric signals. Initially, at sub-operation 502, the denoised combined biometric signal is identified, as processed and outputted from the preceding operations 310, 320, and 330 of method 300. At sub-operation 520, the QRS complex features of the signals are identified to determine the graphical deflections (wherein Q and S are valleys and R is a peak) representative of the depolarization of the left and right ventricles of the user's heart. Once the QRS complex features are identified, one or more of three different feature extraction operations may be performed. That is, method 500 can be used to identify wavelet transformation features of the denoised combined biometric signals at sub-operation 510, wave magnitude features (including without limitation various fiducial point features) relative to the QRS complex features and related wave features at sub-operation 530, and periodicity interval features relative to the QRS complex features and related wave features at sub-operation 540. In an implementation, that is, method 500 may be completed by performing one only of the three aforesaid sub-operations, by performing a combination of any two of them, or by performing all three. Notwithstanding the foregoing, it is likely that the most accurate results for method 300 are obtained by performing all three of the aforesaid sub-operations. In an implementation, the extracted features are normalized after they are identified so that the signals may subsequently be compared based on the same periodicity. The extracted features can be used to, for example, detect a certain disease based on certain rules.

It will be apparent to one skilled in the art in view of the present disclosure that the wavelet transformation features may be identified along with other frequency domain features (including without limitation auto-correlation discrete cosine transform features), which may be identified directly from the thus processed ECG and PO signals denoised in operation 320 and combined in operation 330. That is, in an implementation, the wavelet transformation features and other frequency domain features may be identified separately from the temporal domain features of the combined biometric signals (e.g., wave magnitude features, periodicity interval features, and other fiducial point features), which temporal domain features are identified, for example, based on the identification and detection of the QRS complex features in sub-operation 510.

Figure 6:
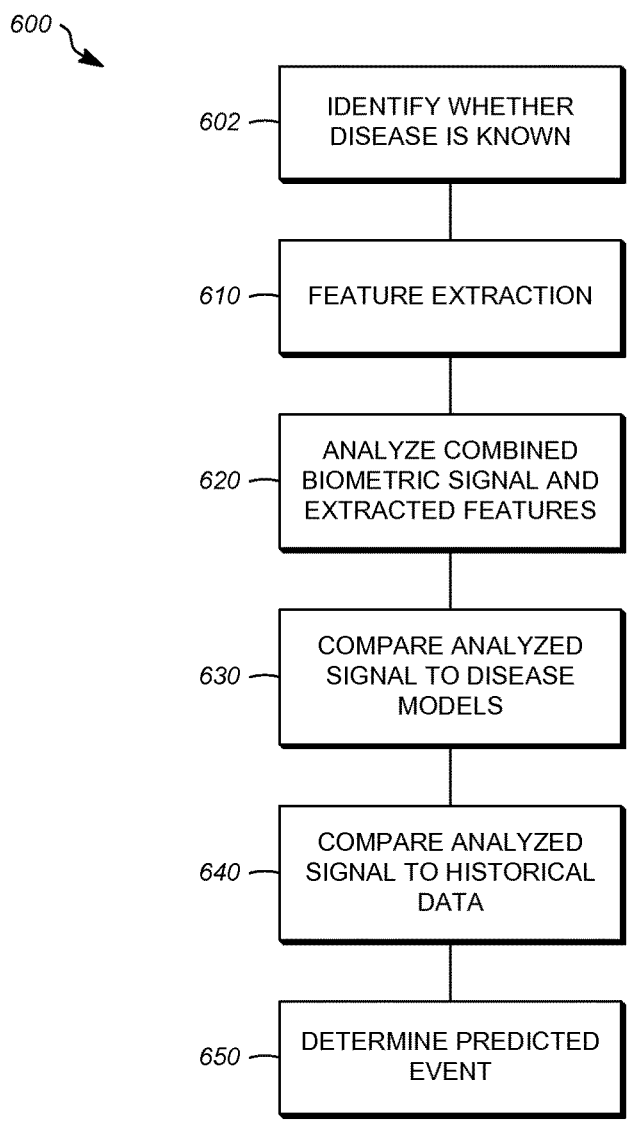
FIG. 6 is a flow chart showing an example of a process of event prediction according to implementations of this disclosure.

At operation 360, a predicted event is determined to identify, for example, disease risk factors and/or disease diagnoses for the user based on the combined biometric signals. FIG. 6 is a flow chart showing an example of a method 600 for event prediction based on the combined biometric signals. If the user is known to have or have had a disease related to the underlying biometric measurement data, this information can be used in the subsequent analysis, for example, by analyzing the combined measurement signals against historical biometric signal data collected from the user. At sub-operation 602, it is determined whether there is a record of the user having a disease that can be identified using an ECG or PO. At sub-operation 610, feature extraction similar to that described above with respect to operation 500 and FIG. 5 may be used to further refine the ECG and PO signals prior to comparing same against disease models. Different disease models may be utilized based on a known disease was identified at sub-operation 602, which disease models may be created or refined during offline training at operation 350 of FIG. 3. The offline training can be based on, for example, labeled data from feature extraction. At sub-operation 620, the combined biometric signal is then analyzed based in part on whether there is a known disease, and, if so, the nature of that disease and the types of biometric data relevant thereto. One or more disease models may be compared against the resulting analyzed signal at sub-operation 630, for example, to determine the likelihood of certain disease factors or the presence thereof. For example, the analysis may be used to diagnosis the user with or monitor the user's prior diagnosis of sleep apnea by identifying periods wherein the user ceases to breath properly while sleeping and other medical conditions such as heart attack, congestive heart failure, chronic obstructive pulmonary disease (COPD), anemia, lung cancer, asthma, or pneumonia. An additional analysis may be conducted at sub-operation 640 to compare the analyzed signal against historical ECG signal data, historical PO signal data, and/or historical combined biometric data, which may provide further insight for indicating disease factors or diagnoses for the user. If the user has previously been diagnosed with a relevant disease or medical condition, the comparison can be used to identify the user's treatment progress and other developments in treatment. Based on the results of the analyses and comparisons, an event relating, for example, to disease diagnosis or prevention can be predicted at sub-operation 650.

At operation 370, multi-modal decision fusion is used to determine the identity of the user based on the measured ECG and PO signals and the analysis completed during operation 360. Ideally, biometric characteristics are unique in that no two individuals have identical measurements therefor and are permanent in that the characteristics do not change over time. However, certain types of biometric characteristics, such as measurements identified via ECG signals, may be insufficient on their own for determining a user's identity, as the measurements may only identify certain qualities of the characteristic, which may be common in many individuals. As such, by utilizing the ECG signals and PO signals from the user, the identification described herein combines multiple different biometric signals from respective sensors to more accurately determine the user's identity. In one implementation, the measured ECG and PO signals may be compared against historical signal records for the user to analyze similarities therein. If it is determined that the measured signals match the historical signal records, the user's identity may be verified.

As used herein, information, signals, or data are received by transmission or accessing the information, signals, or data in any form, such as receiving by transmission over a network, receiving by accessing from a storage device, or receiving by user operation of an input device.

The foregoing description describes only some exemplary implementations of the described techniques. Other implementations are available. For example, the particular naming of the components, capitalization of terms, the attributes, data structures, or any other programming or structural aspect is not mandatory or significant, and the mechanisms that implement the systems and methods described herein or their features may have different names, formats, or protocols. Further, the system may be implemented via a combination of hardware and software, as described, or entirely in hardware elements. Also, the particular division of functionality between the various system components described herein is merely exemplary, and not mandatory; functions performed by a single system component may instead be performed by multiple components, and functions performed by multiple components may instead performed by a single component.

The word "example" is used herein to mean serving as an example, instance, or illustration. Any aspect or design described herein as "example" is not necessarily to be construed as preferred or advantageous over other aspects or designs. Rather, use of the word "example" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an implementation" or "one implementation" throughout is not intended to mean the same implementation unless described as such.

The implementations of the computer devices (e.g., clients and servers) described herein can be realized in hardware, software, or any combination thereof. The hardware can include, for example, computers, intellectual property (IP) cores, application-specific integrated circuits (ASICs), programmable logic arrays, optical processors, programmable logic controllers, microcode, microcontrollers, servers, microprocessors, digital signal processors or any other suitable circuit. In the claims, the term "processor" should be understood as encompassing any of the foregoing hardware, either singly or in combination. Further, portions of each of the clients and each of the servers described herein do not necessarily have to be implemented in the same manner.

Operations that are described as being performed by a single processor, computer, or device can be distributed across a number of different processors, computers or devices. Similarly, operations that are described as being performed by different processors, computers, or devices can, in some cases, be performed by a single processor, computer or device.

Although features may be described above or claimed as acting in certain combinations, one or more features of a combination can in some cases be excised from the combination, and the combination may be directed to a sub-combination or variation of a sub-combination.

The systems described herein, such as client computers and server computers, can be implemented using general purpose computers/processors modified with a computer program that, when executed, carries out any of the respective methods, algorithms and/or instructions described herein. In addition or alternatively, for example, special purpose computers/processors can be utilized which can contain specialized hardware for carrying out any of the methods, algorithms, or instructions described herein.

Some portions of above description include disclosure presented in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times, to refer to these arrangements of operations as modules or by functional names, without loss of generality. It should be noted that the process steps and instructions of implementations of this disclosure could be embodied in software, firmware or hardware, and when embodied in software, could be downloaded to reside on and be operated from different platforms used by real time network operating systems.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

At least one implementation of this disclosure relates to an apparatus for performing the operations herein. This apparatus may be specially constructed for the required purposes, or it may comprise a general-purpose computer selectively activated or reconfigured by a computer program stored on a computer readable storage medium that can be accessed by the computer.

Certain portions of the implementations of the disclosure can take the form of a computer program product accessible from, for example, a non-transitory computer-usable or computer-readable medium. The computer program, when executed, can carry out any of the respective techniques, algorithms and/or instructions described herein. A non-transitory computer-usable or computer-readable medium can be any device that can, for example, tangibly contain, store, communicate, or transport the program for use by or in connection with any processor. The non-transitory medium can be, for example, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for tangibly containing, storing, communicating, or transporting electronic instructions.

It is to be understood that the disclosure is not to be limited to the disclosed implementations but, on the contrary, is intended to cover various modifications and equivalent arrangements included within the scope of the appended claims.

What is claimed is:

1. A method for analysis and prediction of disease risk factors or disease diagnoses of a user of a wearable device based on biometric data generated at the wearable device and communicated to a cloud server using a monitor device intermediate to the wearable device and the cloud server, the method comprising:
    generating, at the wearable device, at least one electrocardiograph (ECG) signal and at least one pulse oximeter (PO) signal associated with the user of the wearable device, wherein the wearable device is defined by a ring body having an interior surface and an exterior surface, wherein the at least one ECG signal is generated responsive to the user contacting a portion of the exterior surface using a first finger of the user while the interior surface is in communication with a second finger of the user;
    outputting the at least one ECG signal and the at least one PO signal to a display of the wearable device;
    transmitting the at least one ECG signal and the at least one PO signal from the wearable device to the monitor device using a short range wireless connection established between the wearable device and the monitor device;
    responsive to the monitor device receiving the at least one ECG signal and the at least one PO signal using the short range wireless connection, processing the at least one ECG signal and the at least one PO signal at the monitor device by:
        performing, at the monitor device, pre-processing on the at least one ECG signal and the at least one PO signal to denoise the at least one ECG signal and to denoise the at least one PO signal; and
        combining, at the monitor device, the pre-processed at least one ECG signal and the pre-processed at least one PO signal into a combined biometric signal;
    outputting the pre-processed at least one ECG signal, the pre-processed at least one PO signal, and the combined biometric signal to a display of the monitor device;
    transmitting the combined biometric signal from the monitor device to the cloud server; and
    responsive to the cloud server receiving the combined biometric signal from the monitor device, analyzing the combined biometric signal at the cloud server to determine at least one predicted event for the user of the wearable device by:
        performing, at the cloud server, feature extraction against the combined biometric signal to determine one or more extracted wave features of the combined biometric signal; and
        determining, at the cloud server, the at least one predicted event associated with the user based on the one or more extracted wave features and based on one or more disease models corresponding to the disease risk factors or the disease diagnoses of the user of the wearable device; and
    storing, at the cloud server, data indicative of the at least one predicted event.

2. The method of claim 1, wherein performing the pre-processing on the at least one ECG signal and the at least one PO signal to denoise the at least one ECG signal and to denoise the at least one PO signal comprises:

removing a baseline wander from a signal, wherein the signal is at least one of the at least one ECG signal or the at least one PO signal;
applying a band-pass filter to the signal;
detecting a periodicity of the signal; and
applying an adaptive motion noise reduction filter to the signal.

3. The method of claim 1, wherein performing the feature extraction against the combined biometric signal to determine the one or more extracted wave features of the combined biometric signal comprises:
identifying QRS complex features of the combined biometric signal; and
identifying each of:
wavelet transformation features of the combined biometric signal;
wave magnitude features relative to the QRS complex features and related wave features; and
periodicity interval features relative to the QRS complex features and related wave features,
wherein the one or more extracted wave features comprise the at least one of the wavelet transformation features, the wave magnitude features, and the periodicity interval features identified.

4. The method of claim 1, wherein determining the at least one predicted event associated with the user based on the one or more extracted wave features and based on one or more disease models corresponding to the disease risk factors or the disease diagnoses of the user of the wearable device comprises:
analyzing, at the cloud server, the combined biometric signal and the one or more extracted wave features to present an analyzed signal;
determining, at the cloud server, a first result by comparing the analyzed signal to the one or more disease models;
determining, at the cloud server, a second result by comparing the analyzed signal to previously stored data, wherein the previously stored data is stored at the cloud server and includes at least one of historical ECG signal data, historical PO signal data, and historical combined biometric signal data; and
determining, at the cloud server, the at least one predicted event based on the first result and the second result.

5. The method of claim 1, further comprising:
extracting, at the wearable device, the at least one ECG signal responsive to the user contacting the portion of the exterior surface of the ring body using the first finger of the user.

6. The method of claim 1, further comprising:
determining, by a multi-modal decision fusion performed at the cloud server, an identity of the user.

7. An apparatus for analysis and prediction of disease risk factors or disease diagnoses of a user of a wearable device based on biometric data generated at the wearable device and communicated to a cloud server using the apparatus, wherein the apparatus is intermediate to the wearable device and the cloud server, the apparatus comprising:
a display;
a non-transitory memory; and
a processor configured to execute instructions stored in the non-transitory memory to:
receive, using a short range wireless connection established between the wearable device and the apparatus, at least one electrocardiograph (ECG) signal and at least one pulse oximeter (PO) signal associated with a user from the wearable device, wherein the wearable device is defined by a ring body having an interior surface and an exterior surface, wherein the at least one ECG signal is generated responsive to the user contacting a portion of the exterior surface using a first finger of the user while the interior surface is in communication with a second finger of the user, wherein the at least one ECG signal and the at least one PO signal are output to a wearable device display;
perform pre-processing on the at least one ECG signal and the at least one PO signal to denoise the at least one ECG signal and to denoise the at least one PO signal;
combine the pre-processed at least one ECG signal and the pre-processed at least one PO signal into a combined biometric signal;
output the pre-processed at least one ECG signal, the pre-processed at least one PO signal, and the combined biometric signal to the display; and
transmit the combined biometric signal to the cloud server, wherein the cloud server analyzes the combined biometric signal to determine at least one predicted event for the user of the wearable device and stores data indicative of the at least one predicted event by:
performing feature extraction against the combined biometric signal to determine one or more extracted wave features of the combined biometric signal;
determining the at least one predicted event associated with the user based on the one or more extracted wave features and based on one or more disease models corresponding to the disease risk factors or the disease diagnoses of the user of the wearable device; and
storing data indicative of the at least one predicted event.

8. The apparatus of claim 7, wherein the instructions to perform the pre-processing on the at least one ECG signal and the at least one PO signal to denoise the at least one ECG signal and to denoise the at least one PO signal comprise instructions to:
remove a baseline wander from a signal, wherein the signal is at least one of the at least one ECG signal or the at least one PO signal;
apply a band-pass filter to the signal;
detect a periodicity of the signal; and
apply an adaptive motion noise reduction filter to the signal.

9. The apparatus of claim 7, wherein the cloud server performs the feature extraction against the combined biometric signal to determine the one or more extracted wave features of the combined biometric signal by:
identifying QRS complex features of the combined biometric signal; and
identifying each of:
wavelet transformation features of the combined biometric signal;
wave magnitude features relative to the QRS complex features and related wave features; and
periodicity interval features relative to the QRS complex features and related wave features,
wherein the one or more extracted wave features comprise the at least one of the wavelet transformation features, the wave magnitude features, and the periodicity interval features identified.

10. The apparatus of claim 7, wherein the cloud server the at least one predicted event associated with the user based on the one or more extracted wave features and based on one or more disease models corresponding to the disease risk factors or the disease diagnoses of the user of the wearable device by:

analyzing the combined biometric signal and the one or more extracted features to present an analyzed signal;

determining a first result by comparing the analyzed signal to the one or more disease models;

determining a second result by comparing the analyzed signal to previously stored data, wherein the previously stored data is stored at the cloud server and includes at least one of historical ECG signal data, historical PO signal data, and historical combined biometric signal data; and determining the at least one predicted event based on the first result and the second result.

11. The apparatus of claim 7, wherein the cloud server is further configured to determine, by a multi-modal decision fusion, an identity of the user.

12. The apparatus of claim 7, wherein the apparatus comprises a monitor device configured to receive the at least one ECG signal and the at least one PO signal from the wearable device.

13. An apparatus for analysis and prediction of disease risk factors or disease diagnoses of a user of the apparatus, comprising:

a wearable ring body having an interior surface and an exterior surface;

a display;

a non-transitory memory;

a processor configured to execute instructions stored in the non-transitory memory to:

identify at least one electrocardiograph (ECG) signal and at least one pulse oximeter (PO) signal associated with a user while the interior surface of the wearable ring body is in communication with a first finger of the user;

output the at least one ECG signal and the at least one PO signal to the display;

perform pre-processing on the at least one ECG signal and the at least one PO signal to denoise the at least one ECG signal and to denoise the at least one PO signal;

combine the pre-processed at least one ECG signal and the pre-processed at least one PO signal into a combined biometric signal;

transmit the pre-processed at least one ECG signal, the pre-processed at least one PO signal, and the combined biometric signal to a monitor device, wherein the monitor device outputs the pre-processed at least one ECG signal, the pre-processed at least one PO signal, and the combined biometric signal at a monitor device display;

perform feature extraction against the combined biometric signal to determine one or more extracted wave features of the combined biometric signal;

determine at least one predicted event associated with the user based on the one or more extracted wave features and based on one or more disease models corresponding to the disease risk factors or the disease diagnoses of the user; and output data indicative of the at least one predicted event to the display; and at least one biometric sensor coupled to a portion of the exterior surface of the wearable ring body to produce the at least one ECG signal associated with the user responsive to the user contacting the portion of the exterior surface of the wearable ring body using a second finger of the user.

14. The apparatus of claim 13, wherein the instructions to perform the pre-processing on the at least one ECG signal and the at least one PO signal to denoise the at least one ECG signal and to denoise the at least one PO signal comprise instructions to:

remove a baseline wander from a signal, wherein the signal is at least one of the at least one ECG signal or the at least one PO signal;

apply a band-pass filter to the signal;

detect a periodicity of the signal; and apply an adaptive motion noise reduction filter to the signal.

15. The apparatus of claim 13, wherein the instructions to perform the feature extraction against the combined biometric signal to determine the one or more extracted features comprise instructions to:

identify QRS complex features of the combined biometric signal; and identify each of:

wavelet transformation features of the combined biometric signal;

wave magnitude features relative to the QRS complex features and related wave features; and periodicity interval features relative to the QRS complex features and related wave features, wherein the one or more extracted wave features comprise the at least one of the wavelet transformation features, the wave magnitude features, and the periodicity interval features identified.

16. The apparatus of claim 13, wherein the instructions to determine the at least one predicted event associated with the user based on the one or more extracted wave features and based on one or more disease models corresponding to the disease risk factors or the disease diagnoses of the user comprise instructions to:

analyze the combined biometric signal and the one or more extracted features to present an analyzed signal;

determine a first result by comparing the analyzed signal to the one or more disease models;

determine a second result by comparing the analyzed signal to previously stored data, wherein the previously stored data includes at least one of historical ECG signal data, historical PO signal data, and historical combined biometric signal data; and determine the at least one predicted event based on the first result and the second result.

17. The apparatus of claim 13, wherein the processor is further configured to execute instructions stored in the non-transitory memory to:

extract the at least one ECG signal responsive to the user contacting the portion of the exterior surface of the wearable ring body using the second finger of the user.

18. The apparatus of claim 13, wherein the processor is further configured to execute instructions stored in the non-transitory memory to:

determine, by a multi-modal decision fusion, an identity of the user.

* * * * *